US005527289A

United States Patent [19]

Foster et al.

[11] Patent Number: 5,527,289
[45] Date of Patent: Jun. 18, 1996

[54] IV MANAGEMENT APPARATUS

[75] Inventors: L. Dale Foster, Brookville; John W. Ruehl, Shelbyville, both of Ind.

[73] Assignee: Hill-Rom Company, Inc., Batesville, Ind.

[21] Appl. No.: 187,223

[22] Filed: Jan. 27, 1994

Related U.S. Application Data

[63] Continuation-in-part of Ser. No. 869,475, Apr. 15, 1992, abandoned.

[51] Int. Cl.$^6$ .......................... A61M 5/142; A61M 5/172
[52] U.S. Cl. ................... 604/151; 128/DIG. 12; 128/DIG. 13
[58] Field of Search .................... 604/151, 141; 128/DIG. 12, DIG. 13

[56] References Cited

U.S. PATENT DOCUMENTS

| | | |
|---|---|---|
| D. 260,816 | 9/1981 | Zissimopoulos . |
| 1,290,809 | 1/1919 | Truax . |
| 1,490,650 | 4/1924 | Wagner . |
| 2,470,524 | 5/1949 | Scudder . |
| 2,673,771 | 3/1954 | Krewson . |
| 2,696,963 | 12/1954 | Shepherd . |
| 3,139,985 | 7/1964 | Sinclair . |
| 3,552,577 | 1/1971 | Latham, Jr. et al. . |
| 3,702,940 | 11/1972 | Stewart . |
| 3,778,232 | 12/1973 | McMorrow, Jr. . |
| 4,225,104 | 9/1980 | Larson . |
| 4,262,872 | 4/1981 | Kodet . |
| 4,352,991 | 10/1982 | Kaufman . |
| 4,511,157 | 4/1985 | Wilt, Jr. . |
| 4,511,158 | 4/1985 | Varga et al. . |
| 4,513,796 | 4/1985 | Miller et al. . |
| 4,559,036 | 12/1985 | Wunsch . |
| 4,600,209 | 7/1986 | Kerr, Jr. . |
| 4,650,464 | 3/1987 | Ruiz ................................ 128/DIG. 13 |
| 4,653,518 | 3/1987 | Adachi . |
| 4,678,460 | 7/1987 | Rosner . |
| 4,712,590 | 12/1987 | Gianfilippo . |
| 4,718,892 | 1/1988 | Yung-Ho . |
| 4,720,768 | 1/1988 | Schindele . |
| 4,729,576 | 3/1988 | Roach . |
| 4,738,368 | 4/1988 | Desjardins . |
| 4,747,826 | 5/1988 | Sassano . |
| 4,795,122 | 1/1989 | Petre . |
| 4,898,578 | 2/1990 | Rubalcaba, Jr. ................ 128/DIG. 13 |
| 4,905,944 | 3/1990 | Jost et al. . |
| 4,925,444 | 5/1990 | Orkin et al. . |
| 4,945,592 | 8/1990 | Sims et al. . |
| 4,946,439 | 8/1990 | Eggers . |
| 4,966,340 | 10/1990 | Hunter . |
| 4,976,687 | 12/1990 | Martin ............................ 128/DIG. 13 |
| 4,993,683 | 2/1991 | Kreuzer . |
| 4,995,432 | 2/1991 | Tervamaki et al. . |
| 5,037,390 | 8/1991 | Raines et al. . |
| 5,100,380 | 3/1992 | Epstein et al. .................. 128/DIG. 13 |
| 5,112,019 | 5/1992 | Metzler et al. . |
| 5,112,319 | 5/1992 | Lai ................................... 128/DIG. 13 |
| 5,167,928 | 12/1992 | Kelly et al. . |
| 5,171,301 | 12/1992 | Vanderveen ............................ 604/153 |
| 5,186,337 | 2/1993 | Foster et al. . |
| 5,207,642 | 5/1993 | Orkin et al. . |
| 5,382,232 | 1/1995 | Hague et al. .................... 128/DIG. 13 |
| 5,417,649 | 5/1995 | Kawahara et al. ............... 128/DIG. 13 |

*Primary Examiner*—Paul J. Hirsch
*Attorney, Agent, or Firm*—Barnes & Thornburg

[57] ABSTRACT

An infusion delivery system eliminates the requirement for individual "smart pump" assemblies each of which includes a processor, power supply and operator I/O for each IV container suspended on an IV rack. An acquisition module capable of supporting multiple IV containers is suspended from the hospital bed frame and includes a plurality of ports into which a connector is inserted for controlling a dumb pump on each IV container. The acquisition module includes a processor, power supply and operator input/output mechanism for programming the delivery schedule for each of several IV containers. The dumb pump on each IV container includes only the mechanical components required for pumping the IV fluid to the patient. The infusion delivery system thus provides a less cluttered, more compact, and economical delivery system for IV fluids compared to the prior art.

17 Claims, 1 Drawing Sheet

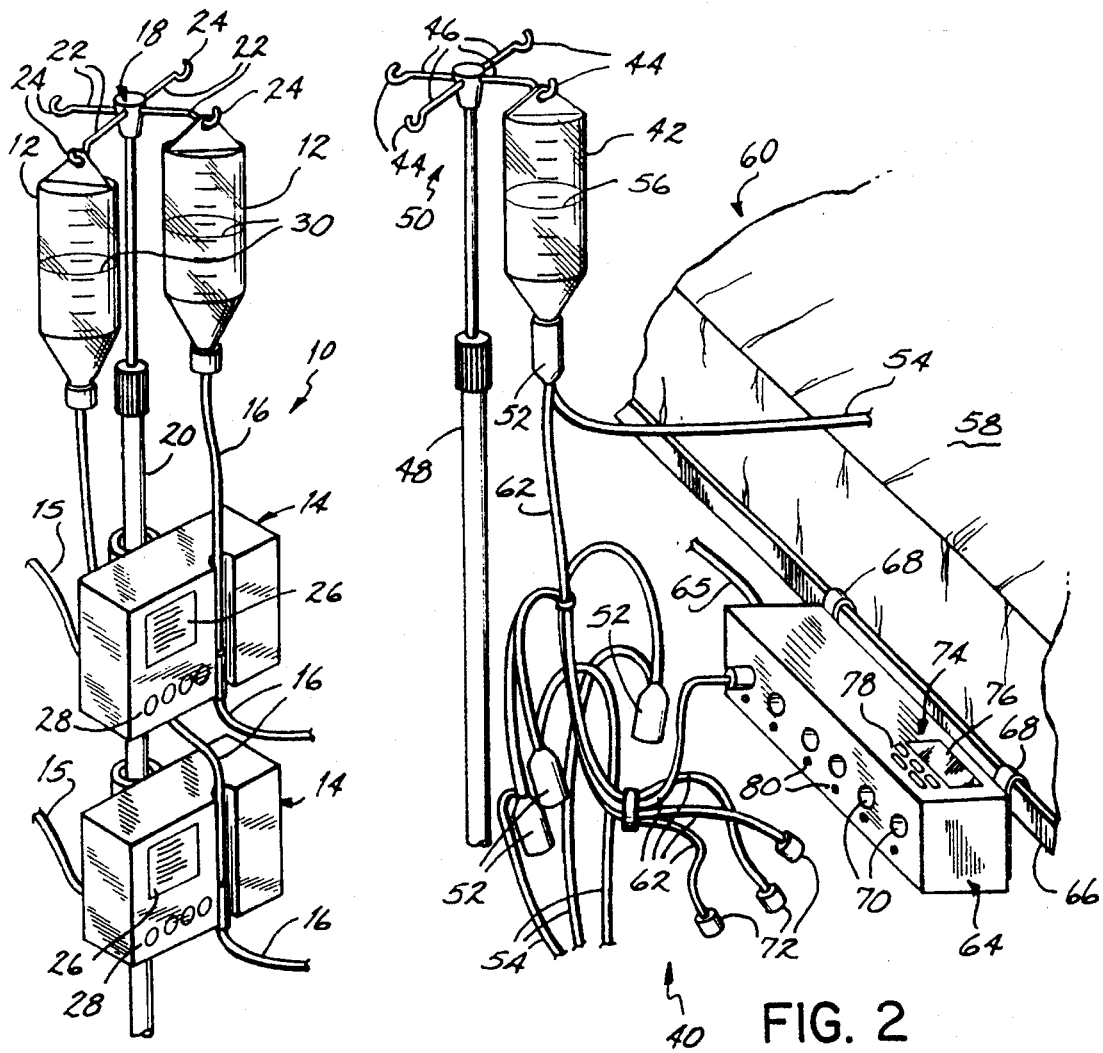
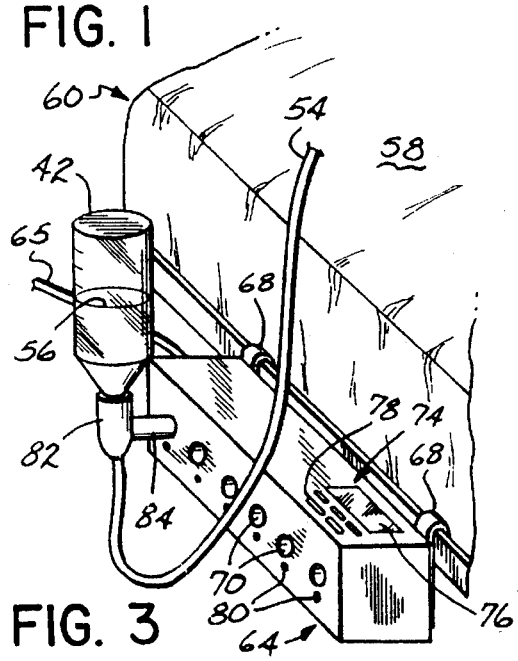
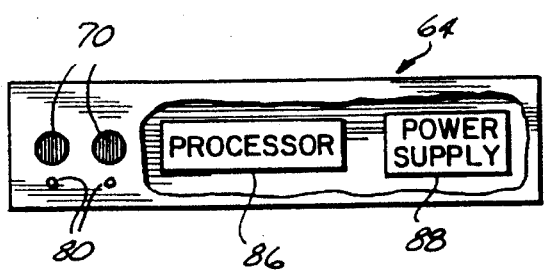
FIG. 1 PRIOR ART
FIG. 2
FIG. 3
FIG. 4

5,527,289

IV MANAGEMENT APPARATUS

RELATED APPLICATIONS

This application is a continuation-in-part application of co-pending application Ser. No. 07/869,475 filed Apr. 15, 1992 now abandoned and assigned to the assignee of the present invention.

FIELD OF THE INVENTION

This invention relates to IV management apparatus, and more particularly to a system for efficiently managing the infusion of multiple IV containers.

BACKGROUND OF THE INVENTION

In critical care situations, an IV rock of the type disclosed in U.S. Pat. No. 4,795,122 is used in order to supply the patient with the multiple fluids that may be required as dictated by the patient's condition. Such fluids include heparin, nitroglycerin, antibiotics, nutrients and the like. In extreme situations, such as those involving bum patients, as many as twelve to fifteen IV infusions with twelve to fifteen separate pump assemblies may be required.

Each pump assembly is connected to an electrical outlet that provides 110 volts to drive the pump assembly. The pump assembly contains a pump, and a DC power supply that is utilized to keep the pump operating when the 110 volt AC power supply is disconnected, as for example, when a patient is transferred from the hospital room to another location in the hospital for diagnosis or treatment.

The current hardware and practices for infusion delivery systems suffer major disadvantages. The multiple connectors joining the pump assemblies to the 110 volt AC outlets add to the general untidiness and complexity of the diagnosis and treatment equipment surrounding the patient and the hospital bed. Furthermore, the power supply, processor, and visual display associated with each pump assembly and IV container substantially increases the required size by way of required volume of space occupied by the pump assembly and its weight and cost of, and difficulty in managing, the infusion delivery system. All of this in turn provides a practical limit for the number of pump assemblies and IV containers to be mounted on a single IV rack. Furthermore, multiple pump assemblies and IV containers must be transported with the movement of the patient from time to time, thereby providing a cumbersome and difficult situation.

SUMMARY OF THE INVENTION

An objective of the present invention has been to provide an infusion delivery system for multiple IV containers wherein the combination is greatly simplified and the occupied volume and weight requirements reduced.

Another objective of this invention has been to provide an improved infusion delivery system wherein a portion of the system is removed from the traditional IV rack and is attached to the hospital bed or other structure for more convenient and less cumbersome and congested operation.

Yet another objective of the present invention has been to ergonomically improve the management of the IV and electrical lines of infusion equipment.

These objectives of the present invention have been attained by providing an infusion delivery system for multiple IV containers wherein m acquisition module is suspended from the hospital bed frame, service cart, or other convenient structure. A pump is connected to each individual IV container and has a connector line attached thereto and an IV line extending therefrom. The connector line has a connector attached to its end for connection to an acquisition module. The IV line delivers the IV fluid from the container to the patient, who is typically situated atop the hospital bed. The pump attached to each IV container mechanically pumps fluid from the container through the IV line; however, the processor, power supply and input/output (I/O) operator control mechanism are all provided on the, acquisition module and not the individual pump. Therefore, the pump attached to each of the individual IV containers is a so-called "dumb pump" as opposed to prior art infusion delivery system "smart pump" assemblies which each have a dedicated power supply, processor, and associated displays and controls for each discrete IV container.

The acquisition module includes multiple ports for inserting individual connectors from each IV container and pump combination. The acquisition module also includes a visual display and keypad entry for programming the delivery schedule and specifications for each port and IV container connected thereto.

Two preferred embodiments are provided. In the first embodiment, the IV container can be suspended from a conventional IV rack; the dumb pump is joined to the connector and hence the acquisition module by the connector line. In the second embodiment, the connector attaches the dumb pump directly to the acquisition module without an IV rack or connector line thereby positioning the IV container proximate the hospital bed along with the acquisition module supported from the bed frame.

An advantage provided by the present invention is the elimination of the tangle of electrical conductors coming from a plurality of so-called "smart pump" assemblies mounted on an IV rack. Furthermore, there is a reduction in the volume occupied and weight of the pumping equipment required for a plurality of IV containers due to the provision of a common power supply processor, display, and I/O operator mechanism on the acquisition module for multiple IV containers. The acquisition module offers less obstruction and a more orderly and downsized infusion delivery system for multiple IV containers.

BRIEF DESCRIPTION OF THE DRAWINGS

The several objectives, features and advantages of this invention will become more readily apparent from the following detailed description taken in conjunction with the accompanying drawings in which:

FIG. 1 is an IV rack with multiple IV containers and an associated smart pump for each container according to the prior art;

FIG. 2 is a diagrammatic perspective view of an IV container and dumb pump suspended from an IV rack and connected to an acquisition module supported on the bed frame of the present invention;

FIG. 3 is a diagrammatic perspective view of an IV container connected directly to the acquisition module supported by the bed frame; and FIG. 4 is a diagrammatic partially sectioned view of the acquisition module.

DETAILED DESCRIPTION OF THE INVENTION

An IV management system 10 according to the prior art is shown in FIG. 1 as having multiple and separate IV containers 12 and m-called "smart pump" assemblies 14. The IV container 12 is connected to an individual smart pump assembly 14 through an IV line 16. The multiple IV containers 12 are suspended on an IV rack 18 including a generally vertical telescoping pole 20 having a plurality of radially extending support arms 22 from which the multiple IV containers 12 are suspended on a hook 24 at the terminal end of each support arm 22. Each IV container 12 is connected to an IV pump assembly 14 suspended on the vertical pole 20 of the IV rack 18. Each pump assembly 14 includes a visual display 26 and keypad entry system 28 for programming the delivery schedule for a volume of IV fluid 30 within the IV container 12. The pump assembly 14 of the prior art includes a pump mechanism (within assembly 14 but not shown), provision, for example a conductor 15, for connecting to a power supply typically consisting of a 110 volt AC wall outlet (not shown), a battery for DC back-up power supply (within assembly 14 but not shown), and a processor (within assembly 14 but not shown). As a result, the IV pump assembly 14 of the prior art is commonly referred to as a "smart pump" assembly. The inclusion of multiple IV containers 12 connected to individual smart pump assemblies 14 suspended on the single IV rack 18 provides a cluttered, heavy and generally untidy IV management system.

A first preferred embodiment of the present invention has an improved infusion delivery system 40 for multiple IV containers. The infusion delivery system 40 of this embodiment shown in FIG. 2 includes an IV container 42 suspended from a hook 44 on the terminal portion of a support arm 46 at the uppermost end of the telescoping vertical pole 48 of an IV rack 50. Connected to each IV container 42 is a "dumb pump" 52 having an IV line 54 extending therefrom for delivering IV fluid 56 within the container 42 to a patient (not shown), who is typically situated atop a mattress 58 on the hospital bed 60. Also attached to the dumb pump 52 is a connector line 62 to link to an acquisition module 64 suspended on a bed frame 66 of the hospital bed 60 by a pair of hooks 68.

The acquisition module 64 includes a plurality of ports 70 into which a connector 72 at the terminal end of each connector line 62 is inserted. The acquisition module 64 includes an operator input/output (I/O) mechanism 74 including a visual display 76 and keypad entry system 78. The operator I/O mechanism 74 enables a care provider to program the specific delivery schedule for the IV fluid 56 in a discreet IV container 42 connected to one of the ports 70 on the acquisition module 64. An indicator light 80, such as an LED, is provided for each port 70 to indicate which port 70 is being programmed or accessed at any given time. Once programmed, each dumb pump 52 operates independently of and simultaneously with respect to all others of the pumps 52, thereby providing continuous, parallel fluid delivery at the appropriate programmed flow rates.

Within the acquisition module 64 is a processor 86 (FIG. 4) and power supply 88 (FIG. 4) to be accessed by the multiple IV containers 42 and dumb pumps 52 through each discrete port 70 and associated connector line 62. As with the prior art, provision for connecting module 64 to a 110 volt AC wall outlet power supply is provided via connector 65 and a DC power supply 88 serves as a back-up power supply within the acquisition module 64.

The dumb pump 52 connected to each IV container 42 includes only the mechanical pumping mechanism required for the delivery of the IV fluid 56. The power supply 88, processor 86, and operator I/O mechanism 74 for each dumb pump 52 is provided in the acquisition module 64 and is accessed through the connector 72 inserted within an individual port 70. As a result, the expensive and bulky smart pump assembly 14 required for each individual IV container 12 in the prior art is eliminated, thereby reducing the overall cost for a multiple IV delivery system and reducing the cluttered and congested configuration of the prior art IV rack 18.

It will be appreciated by one of ordinary skill in the art that although the single IV container 42 is shown suspended on the IV rack 50 in FIG. 2, multiple IV containers 42 can be supported on the IV rack 50 and managed by the acquisition module 64 according to the present invention.

A second preferred embodiment of this invention is shown in FIG. 3 with the same reference numerals indicating similar components as in the first embodiment shown in FIG. 2. In the second embodiment an IV rack is not required in that the IV container 42 is supported directly on the acquisition module 64 through a dumb pump 82 with a connector 84 inserted directly into the port 70 on the acquisition module 64. The connector line 62 as employed in the first embodiment of this invention is not required. The IV line extends directly from the dumb pump 82 to the patient as in the first embodiment. With the second embodiment as shown in FIG. 3, the infusion delivery system of this invention can be more conveniently transported with a patient in the hospital bed 60 without disrupting the delivery of IV fluids 56. The IV rack as shown in FIGS. 1 and 2 is not required to be trailed along with the hospital bed 60 when the patient is transported from the hospital room in that the acquisition module 64 and multiple IV containers 42 and associated dumb pumps 82 are suspended from the bed frame 66 and accompany the patient to maintain the delivery of IV fluids 56. As in the first embodiment of this invention, once programmed, each dumb pump 82 operates independently of and simultaneously with respect to all others of the pumps 82, thereby providing continuous, parallel fluid delivery at the appropriate programmed flow rates.

From the above disclosure of the general principles of the present invention and the preceding detailed description of preferred embodiments, those skilled in the art will readily comprehend the various modifications to which the present invention is susceptible. Therefore, we desire to be limited only by the scope of the following claims.

We claim:

1. An infusion delivery system comprising:

a rack for supporting a plurality of IV containers;

a dumb pump operatively connected to each said IV container, each said pump having a connector attached thereto and an IV line extending therefrom, said IV line being operable to deliver IV fluid from said IV container to a patient; and an acquisition module for controlling a plurality of said pumps, said module including a plurality of ports, each said port adapted to have connected thereto one of said connectors, said module including a processor for control of each said pump.

2. The system of claim 1 wherein said acquisition module includes a power supply.

3. The system of claim 1 wherein said acquisition module includes an operator I/O mechanism.

4. The system of claim 3 wherein said operator I/O mechanism includes a display to indicate the status of a selected said port and said pump connected thereto.

5. The system of claim 3 wherein said operator I/O mechanism includes a keypad entry system for programming said processor to control each said port and said pump connected thereto.

6. The system of claim 3 wherein said operator I/O mechanism includes a display to indicate the status of a selected said port and said pump connected thereto, and a keypad entry system for programming said processor to control each said port and said pump connected thereto.

7. The system of claim 1 wherein said acquisition module is supported on a frame of a hospital bed.

8. The system of claim 1 wherein each said pump operates independently and simultaneously with respect to others of said pumps.

9. An infusion delivery system comprising:

at least one IV container;

a dumb pump operatively connected to each said IV container, each said pump having a connector attached thereto and an IV line extending therefrom, said IV line being capable of delivering IV fluid from said IV container to a patient; and an acquisition module for controlling a plurality of said pumps, said module including a plurality of ports, each said port adapted to have connected thereto one of said connectors, said module including a processor for control of each said pump, said acquisition module and each combination of said connector, said pump and said IV container being attached to said module which is supported on a frame of a hospital bed.

10. The system of claim 9 wherein said acquisition module includes a power supply.

11. The system of claim 9 wherein said acquisition module includes an operator I/O mechanism.

12. The system of claim 11 wherein said operator I/O mechanism includes a display to indicate the status of a selected said port and said pump connected thereto.

13. The system of claim 11 wherein said operator I/O mechanism includes a keypad entry system for programming said processor to control each said port and said pump connected thereto.

14. The system of claim 11 wherein said operator I/O mechanism includes a display to indicate the status of a selected said port and said pump connected thereto, and a keypad entry system for programming said processor to control each said port and said pump connected thereto.

15. The system of claim 9 wherein each said pump operates independently and simultaneously with respect to others of said pumps.

16. An infusion delivery system comprising:

a plurality of IV containers;

a dumb pump operatively connected to each said IV container, each said pump having a connector attached thereto and an IV line extending therefrom, said IV line being operable to deliver IV fluid from said IV container to a patient; and an acquisition module for controlling a plurality of said pumps, said module being supported on a frame of a hospital bed and including a plurality of ports, a processor, a power supply, a single display and a single entry system, each said port adapted to have connected thereto one of said connectors, said processor controlling each said pump, said display indicating the status of a selected said port and said pump connected thereto, and said entry system enabling a health care provider to program said processor to individually control each said port and said pump connected thereto.

17. An infusion delivery system comprising:

at least one IV container;

a dumb pump operatively connected to each said IV container, each said pump having a connector attached thereto and an IV line extending therefrom, said IV line being operable to deliver IV fluid from said IV container to a patient; and an acquisition module for controlling a plurality of said pumps, said module including a plurality of ports, a processor, a power supply, a single display and a single entry system, each said port adapted to have connected thereto one of said connectors, said processor controlling each said pump, said display indicating the status of a selected said port and said pump connected thereto, and said entry system enabling a health care provider to program said processor to control each said port and said pump connected thereto, said acquisition module and each combination of said connector, said pump and said IV container being attached to said module which is supported on a frame of a hospital bed.

* * * * *